(12) United States Patent
Roszell et al.

(10) Patent No.: US 8,128,913 B1
(45) Date of Patent: Mar. 6, 2012

(54) SUNSCREEN COMPOSITION WITH ENHANCED UV-A ABSORBER STABILITY AND METHODS

(75) Inventors: James A. Roszell, Henderson, NV (US); Jie Zhang, Henderson, NV (US)

(73) Assignee: Skinvisible Pharmaceuticals, Inc., Las Vegas, NV (US)

( * ) Notice: Subject to any disclaimer, the term of this patent is extended or adjusted under 35 U.S.C. 154(b) by 337 days.

(21) Appl. No.: 12/316,121

(22) Filed: Dec. 8, 2008

Related U.S. Application Data

(60) Provisional application No. 61/005,863, filed on Dec. 6, 2007.

(51) Int. Cl.
*A61K 8/00* (2006.01)
*A61K 8/18* (2006.01)
*A61Q 17/04* (2006.01)

(52) U.S. Cl. .......................................................... 424/59

(58) Field of Classification Search .................. None
See application file for complete search history.

(56) References Cited

U.S. PATENT DOCUMENTS

| | | | |
|---|---|---|---|
| 3,817,887 A | 6/1974 | Mestetsky |
| 4,035,506 A | 7/1977 | Lucas et al. |
| 4,301,145 A | 11/1981 | Cestari |
| 4,448,906 A | 5/1984 | Deinet et al. |
| 4,500,338 A | 2/1985 | Young et al. |
| 4,507,279 A | 3/1985 | Okuyama et al. |
| 4,645,794 A | 2/1987 | Davis et al. |
| 4,671,957 A | 6/1987 | Holtshousen |
| 4,803,066 A | 2/1989 | Edwards |
| 4,810,489 A | 3/1989 | Murray et al. |
| 4,840,687 A | 6/1989 | Forsberg et al. |
| 4,897,259 A | 1/1990 | Murray et al. |
| 4,971,800 A | 11/1990 | Chess et al. |
| 5,019,604 A | 5/1991 | Lemole |
| 5,045,317 A | 9/1991 | Chess et al. |
| 5,051,260 A | 9/1991 | Chess et al. |
| 5,055,303 A | 10/1991 | Riley, Jr. |
| 5,082,656 A | 1/1992 | Hui et al. |
| 5,126,136 A | 6/1992 | Merat et al. |

(Continued)

FOREIGN PATENT DOCUMENTS

EP 640352 3/1995
(Continued)

OTHER PUBLICATIONS http://en.wikinedia.org/wiki/Parsol_1789 (avobenzone), 3 pgs.

(Continued)

*Primary Examiner* — Johann Richter
*Assistant Examiner* — Thor Nielsen
(74) *Attorney, Agent, or Firm* — Merchant & Gould, P.C.

(57) ABSTRACT

A sunscreen composition is provided according to the present invention. The sunscreen composition includes a skin bonding polymer composition comprising a hydrophobic polymer/hydrophilic polymer adduct, at least one sunscreen active agent comprising a UV-A absorber, and water in an amount of affected to provide a the composition with the texture suitable for application to skin. The hydrophobic polymer/hydrophilic polymer adduct comprises: (i) hydrophobic polymer composition comprising a mixture of a lower poly(vinylpyrrolidone/alkylene) polymer wherein the alkylene group contains about 10 to about 24 carbon atoms and a higher poly(vinylpyrrolidone/alkylene) polymer wherein the alkylene group contains greater than about 24 carbon atoms; and (ii) hydrophilic polymer composition comprising carboxylic acid groups, hydroxyl groups, or both carboxylic acid groups and hydroxyl groups.

19 Claims, 2 Drawing Sheets

U.S. PATENT DOCUMENTS

| | | | |
|---|---|---|---|
| 5,155,199 | A | 10/1992 | Hayashi |
| 5,232,691 | A | 8/1993 | Lemole |
| 5,266,329 | A | 11/1993 | Riley, Jr. |
| 5,298,534 | A | 3/1994 | Prosise et al. |
| 5,320,838 | A | 6/1994 | Woller |
| 5,336,305 | A | 8/1994 | Staats |
| 5,370,876 | A | 12/1994 | Noll et al. |
| 5,389,363 | A | 2/1995 | Snyder et al. |
| 5,417,968 | A | 5/1995 | Staats |
| 5,431,756 | A | 7/1995 | Kosowski et al. |
| 5,486,352 | A | 1/1996 | Guerrero |
| 5,508,024 | A | 4/1996 | Tranner |
| 5,518,712 | A | 5/1996 | Stewart |
| 5,597,849 | A | 1/1997 | McGinity et al. |
| 5,605,676 | A | 2/1997 | Gaffar et al. |
| 5,607,979 | A | 3/1997 | McCreery |
| 5,622,993 | A | 4/1997 | McGinity et al. |
| 5,658,559 | A | 8/1997 | Smith |
| 5,707,612 | A | 1/1998 | Zofchak et al. |
| 5,721,306 | A | 2/1998 | Tsipursky et al. |
| 5,725,844 | A | 3/1998 | Gers-Barlag et al. |
| 5,725,875 | A | 3/1998 | Noll et al. |
| 5,730,966 | A | 3/1998 | Torgerson et al. |
| 5,736,128 | A | 4/1998 | Chaudhuri et al. |
| 5,747,022 | A | 5/1998 | Slavtcheff |
| 5,807,957 | A | 9/1998 | Samour et al. |
| 5,834,538 | A | 11/1998 | deHullu et al. |
| 5,874,074 | A | 2/1999 | Smith |
| 5,885,557 | A | 3/1999 | Lentini |
| 5,891,470 | A | 4/1999 | Rinaldi et al. |
| 5,906,822 | A | 5/1999 | Samour et al. |
| 5,911,980 | A | 6/1999 | Samour et al. |
| 5,916,541 | A * | 6/1999 | Stewart ........................ 424/59 |
| 5,939,453 | A | 8/1999 | Heller et al. |
| 5,942,545 | A | 8/1999 | Samour et al. |
| 5,955,109 | A | 9/1999 | Won et al. |
| 5,968,543 | A | 10/1999 | Heller et al. |
| 5,968,919 | A | 10/1999 | Samour et al. |
| 5,976,566 | A | 11/1999 | Samour et al. |
| 5,980,876 | A | 11/1999 | Peffly |
| 6,074,630 | A | 6/2000 | Devillez et al. |
| 6,096,344 | A | 8/2000 | Liu et al. |
| 6,177,068 | B1 | 1/2001 | Shih et al. |
| 6,183,766 | B1 | 2/2001 | Sine et al. |
| 6,190,689 | B1 | 2/2001 | Hoffmann et al. |
| 6,197,281 | B1 | 3/2001 | Stewart et al. |
| 6,255,421 | B1 | 7/2001 | Plochocka et al. |
| 6,429,326 | B1 | 8/2002 | Richard et al. |
| 6,436,376 | B1 | 8/2002 | Hansenne et al. |
| 6,582,683 | B2 | 6/2003 | Jezior |
| 6,583,220 | B1 | 6/2003 | Lipman |
| 6,627,217 | B1 | 9/2003 | Suzuki et al. |
| 6,699,460 | B2 | 3/2004 | Candau |
| 6,699,461 | B2 | 3/2004 | Candau |
| 6,756,059 | B2 | 6/2004 | Roszell et al. |
| 6,881,400 | B2 | 4/2005 | Collin |
| 7,285,262 | B2 | 10/2007 | Lott |
| 2003/0044374 | A1 | 3/2003 | Roszell et al. |
| 2004/0126339 | A1* | 7/2004 | Roszell ........................ 424/59 |
| 2005/0089491 | A1 | 4/2005 | Collin |
| 2005/0118214 | A1 | 6/2005 | Najdek et al. |
| 2010/0173904 | A1* | 7/2010 | Roszell et al. ............. 514/231.2 |

FOREIGN PATENT DOCUMENTS

| | | |
|---|---|---|
| EP | 747062 | 12/1996 |
| EP | 391741 | 4/1998 |
| JP | 7089826 | 4/1995 |
| JP | 10095714 A | 9/1996 |
| JP | 10067618 | 3/1998 |
| JP | 2002104920 | 4/2002 |
| WO | WO 97/42933 | 11/1997 |
| WO | WO 2006/028613 | 3/2006 |
| WO | WO 2006/118638 | 11/2006 |

OTHER PUBLICATIONS http://www.cosmeticsdatabase.com/special/sunscreens/summary.php., Sunscreen Summary—What Works and What's Safe, 11 pags.

Chatelain et al., "Photostabilization of Butyl methoxydibenzoylmethane (Abovenzone) and Ethylhexyl methoxycinnamate by Bis-ethylhexyloxyphenol methoxyphenyl triazine (Tinosorb S), a New UV Broadband Filter," Photochemistry and Photobiology, 2001, 74(3): 401-406.

http://en.wikipedia.or/wiki/Retinoid, 3 pgs.

Declaration of James Roszell dated Oct. 22, 2008.

Bradley, C. et al., "Noninvasive Transdermal Chemical Collection", *Skin Pharmacol*, pp. 218-226 (1990).

Hasirci V., "Synthesis and characterization of PVNO and PVNO-PVP hydrogels", *Biomaterials*, vol. 2, No. 1, 7 pages (Jan. 1981).

Material Safety Data Sheet, Gantrez S-97 BF Solution, ISP Technologies, Inc., 6 pages (Apr. 7, 1994).

Material Safety Data Sheet, Ganez V-216, ISP Technologies, Inc., pp. 5 pages (Sep. 16, 1994).

Material Safety Data Sheet, Ganex V-220, ISP Technologies, Inc., 5 pages (Oct. 7, 1998).

Nair, P. et al., "Studies on the effect of degree of hydrophilicity on tissue response of polyurethane interpenetrating polymer networks", *Biomaterials*, vol. 13, No. 8, pp. 536-542 (1992).

Shinichi, N. et al., "Hair treatment agent-includes specific high molecular copolymer compounds by which skin layer is made to form on hair surface", *Derwent Abstract* (ACC#1998-280363; Week# 199825) (1999).

Tiller et al., "Designing surfaces that kill bacteria on contact", http://www/pnas.org/cgi/content/abstract/98/11/5981, PNAS Online, 2 pages (May 22, 2001).

* cited by examiner

SUNSCREEN COMPOSITION WITH ENHANCED UV-A ABSORBER STABILITY AND METHODS

CROSS REFERENCE TO RELATED APPLICATIONS

This application claims priority to provisional patent application No. 61/005,863 that was filed with the United States Patent and Trademark Office on Dec. 6, 2007. The entire disclosure of U.S. provisional application No. 61/005,863 is incorporated herein in its entirety.

FIELD OF THE INVENTION

The present invention relates to a sunscreen composition, a method for manufacturing a sunscreen composition, and a method for using a sunscreen composition.

BACKGROUND

The undesirable effects of over exposure to sunlight are well known. Such exposure can result in not only uncomfortable sunburn but in prematurely aging skin, wrinkles, loss of skin elasticity, dermatosis, and skin cancer. Sunscreening is desirable in order to protect the skin from these, and other, adverse effects of solar radiation. The most dangerous solar radiation is the ultraviolet (UV) radiation at wave lengths lower than 400 nm which includes both UV-A and UV-B radiation.

Conventional sunscreen compositions are typically in the form of a liquid, either a lotion or a cream. These compositions may be either oil or water based. The water based emulsion serves mainly as an aid to disperse the active ingredients topically. The carrier water evaporates and leaves a thin film of active ingredients plus excipients deposited on the skin. The film remaining on the skin contains the product which protects the skin from ultraviolet radiation. Sunscreen compositions are typically rated by their sun protection factor (SPF) which is a measure of the protection from the sun afforded by the sunscreen agent or composition containing the sunscreen agent. Compositions having higher SPF values provide more protection from solar radiation.

Numerous disclosures of sunscreen compositions are available. For example, see U.S. Patent Publication No. US 2004/0126339 to Roszell, U.S. Pat. No. 5,518,712 to Stewart, U.S. Pat. No. 5,916,541 to Stewart, International Publication No. WO 97/42933 to Stewart, U.S. Pat. No. 6,074,630 to Devillez et al., U.S. Pat. No. 5,885,557 to Lentini, and U.S. Pat. No. 6,436,376 to Hansenne et al.

Sunscreen agents that primarily filter or absorb UV-A light are often referred to as UV-A absorbers. Similarly, sunscreen agents that primarily filter or absorb UV-B light are often referred to as UV-B absorbers. In general, the UV-A light refers to ultraviolet light having a wave length of 320-400 nm and UV-B light refers to ultraviolet light have a wave length of 280-320 nm.

UV-A absorbers have a tendency to degrade when exposed to light. For example, the UV-A absorber avobenzone (available under the name Parsol 1789) is known to degrade when exposed to light. See http://en.wikipedia.org/wiki/Parsol_1789 (avobenzone). A variety of ingredients have been proposed to enhance the photo stability of avobenzone, including Croda's new Optisol, and Ciba's Tinosorb S (Photochemistry and Photobiology, 2001, 74(3): 401-406). The photo stability of avobenzone remains highly formulation dependent. See http://www.cosmeticsdatabase.com/special/sunscreens/summary.php.

SUMMARY

A sunscreen composition that provides stability to a UV-A absorber is described. The sunscreen composition includes a skin bonding polymer composition comprising a hydrophobic polymer/hydrophilic polymer adduct, at least one sunscreen active agent comprising a UV-A absorber, and water in an amount of affected to provide a the composition with the texture suitable for application to skin. The hydrophobic polymer/hydrophilic polymer adduct comprises: (i) hydrophobic polymer composition comprising a mixture of a lower poly(vinylpyrrolidone/alkylene) polymer wherein the alkylene group contains about 10 to about 24 carbon atoms and a higher poly(vinylpyrrolidone/alkylene) polymer wherein the alkylene group contains greater than about 24 carbon atoms; and (ii) hydrophilic polymer composition comprising carboxylic groups, hydroxylic groups, or both carboxylic groups and hydroxylic groups.

Methods of making and using a sunscreen composition are described.

DETAILED DESCRIPTION

Figure 1:
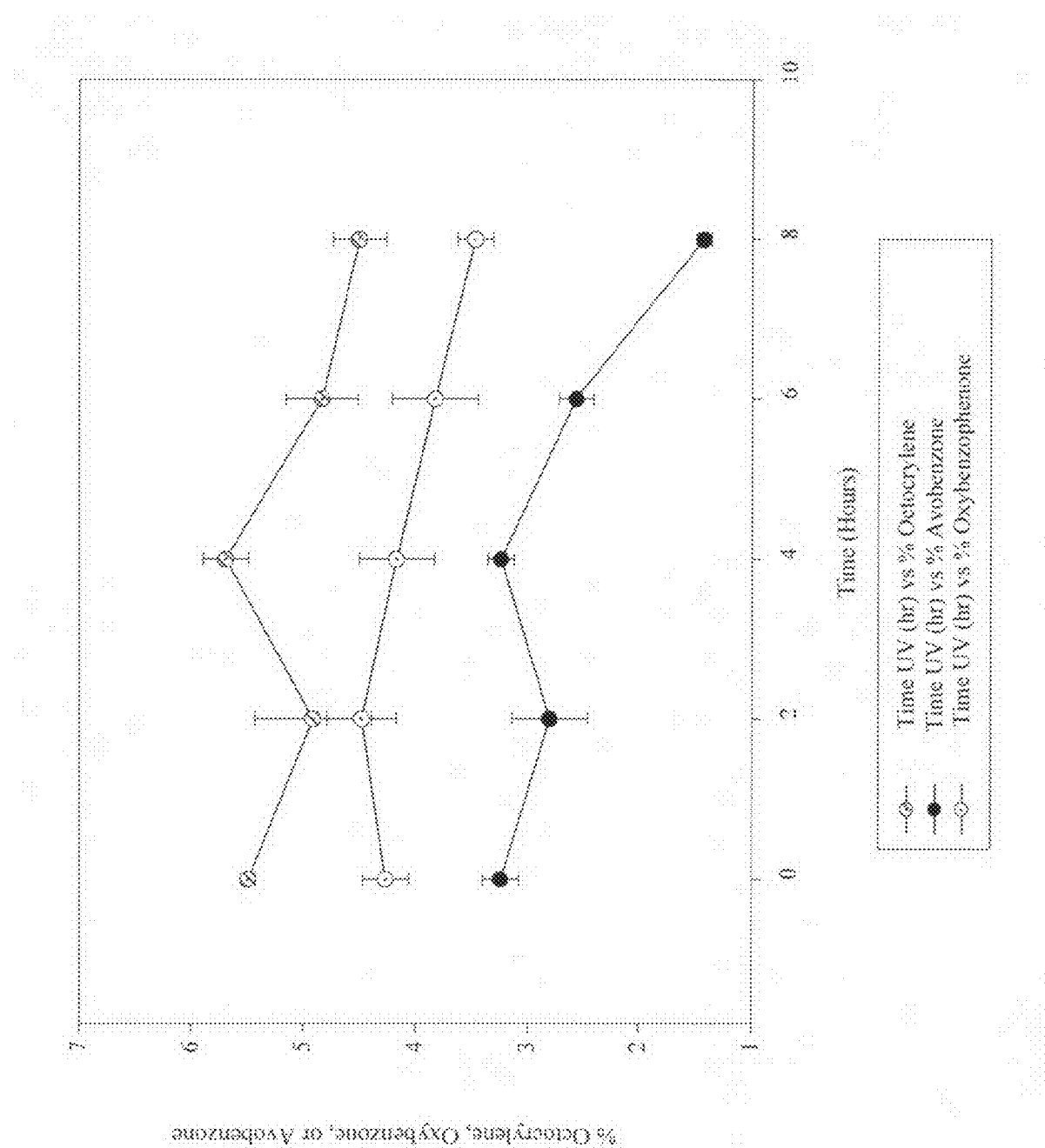
FIG. 1 is a graph of photostability of oxybenzophenone, octocrylene, and avobenzone with UV exposure.

A sunscreen composition is composition that, when applied to skin, protects the skin from ultraviolet radiation from the sun. The sunscreen composition can be referred to more simply as a sunscreen or as a composition.

The sunscreen composition includes a sunscreen agent, a skin bonding polymer composition, and water. The sunscreen composition can include additional components commonly found in sunscreens composition including, for example, surfactants, pH adjusting agents, thickeners, emollients, moisturizers, coloring agents, preservatives, antioxidants, chelating agents, and fragrances.

The sunscreen agent includes a UV-A absorber. In general, certain UV-A absorbers, such as oxybenzophenone and avobenzone have a tendency to lose effectiveness as a UV-A absorber as a result of exposure to light. Octocrylene is a UV-B absorber that provides some UV-A absorptions (is sometimes characterized as a UV-A absorber) but tends to lose effectiveness as a UV-A absorber as a result of expose to light. The skin bonding polymer composition that is provided as part of the sunscreen composition can be constructed to enhance the stability of the UV-A absorber so that the sunscreen composition provides protection against UV-A for a longer period of time compared with sunscreen compositions that do not enhance the stability of the UV-A absorber. In general, a UV-A absorber refers to a component having a primary or maximum UV absorption in the UV-A range of 320-400 nm. A UV-B absorber refers to a component having a primary or maximum UV absorption in the UV-B range of 280-320 nm. The maximum or primary UV absorbance refers to the wave length at which a maximum amount of light is absorbed. The characterization can be evaluated by running a UV spectrum.

The sunscreen composition can be applied by hand application to skin tissue. In general, hand application refers to rubbing the sunscreen composition on to skin tissue by use of a hand.

Skin Bonding Polymer Component

The sunscreen composition can include a skin bonding polymer component. The skin bonding polymer component can include any polymer that, when applied to the skin, helps hold the sunscreen agent to the skin. The skin bonding polymer component holds the sunscreen agent in proximity to skin tissue when applied to the skin tissue so that the sunscreen agent can protect the skin tissue from solar radiation. The skin bonding polymer component can be referred to as the polymer component. The polymer component can be provided as a polymer having an average molecular weight of at least about 2,000. The polymer component can be provided as a polymer having an average molecular weight of less than about 500,000.

The sunscreen composition can bind or adhere to skin tissue for a length of time, and can hold or contain the sunscreen agent within the composition. It is expected that the sunscreen composition is able to adhere or bind to skin tissue for at least about four hours and hold the sunscreen agent contained therein in proximity to skin tissue for at least that length of time.

The polymer component can be prepared from a topical composition precursor that can be prepared by melt processing a hydrophobic polymer composition and a hydrophilic polymer composition to provide an interaction between the hydrophobic polymer composition and the hydrophilic polymer composition. It should be understood that the phrase "melt processing" refers to mixing the hydrophobic polymer composition and the hydrophilic polymer composition under conditions that provide that the hydrophobic polymer component of the hydrophobic polymer composition and the hydrophilic polymer component of the hydrophilic polymer composition are in a liquid state so that they sufficiently mix. When the polymers are sufficiently mixed, it is believed that an interaction forms between the hydrophobic polymer component and the hydrophilic polymer component. The melt processing temperature can be at least about 50° C. and can be at least about 125° C. to generate this interaction.

The interaction exhibited between the hydrophobic polymer component and the hydrophilic polymer component can be characterized as a type of complex formation reaction, and that the complex, once formed, is stable in water at temperatures up to 65° C. and at a pH range of 3.0 to 9.0. By stable, it is meant that the complex does not favor disassociation under these conditions. It is believed that this interaction provides the sunscreen composition with an ability to bind or hold onto the sunscreen agent, allows the sunscreen composition to be emulsified in water, and provides the sunscreen composition with an ability to bind to skin. The result of the interaction between the hydrophobic polymer component and the hydrophilic polymer component can be referred to as a hydrophobic polymer/hydrophilic polymer adduct. It should be understood that the term "adduct" is used to refer to the interaction between the hydrophobic polymer component and the hydrophilic polymer component. The interaction may be a form of complexing, but that is only theory. Accordingly, it should be understood that the term "adduct" is not meant to limit the polymer component to a particular theory of interaction.

It is believed that the interaction between the hydrophobic polymer component and the hydrophilic polymer component can be achieved more easily in the absence of water, or by limiting the presence of water during complex formation. If the hydrophilic polymer component becomes dissolved in water before forming the complex, it can be more difficult to sufficiently mix the hydrophobic polymer component and the hydrophilic polymer component to provide the desired level of interaction. Although a convenient technique for providing the desired level of interaction between the hydrophobic polymer component and the hydrophilic polymer component is melt mixing, it is expected that other techniques can be used to achieve the desired level of interaction.

The hydrophobic polymer composition that can be used according to the invention includes a mixture of hydrophobic polymers. The hydrophobic polymer composition can include components having repeating pyrrolidone/alkylene groups. Exemplary polymers having repeating pyrrolidone/alkylene groups include poly(vinylpyrrolidone/alkylene) polymers. Poly(vinylpyrrolidone/alkylene) polymers include those polymers obtained by polymerizing alkylene substituted vinylpyrrolidone. Poly(vinylpyrrolidone/alkylene) polymers can be represented by the following general formula:

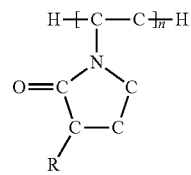

wherein R represents a carbon chain substitute such as an alkylene group and n represents the number of repeating units. The R group is preferably sufficiently long so that the polymer remains relatively water insoluble and should not be too long so that the polymer is too difficult to process. The alkylene group can contain a length of at least about 10 carbon atoms. The mixture of hydrophobic polymers can include a mixture of a lower poly(vinylpyrrolidone/alkylene) polymer and a higher poly(vinylpyrrolidone/alkylene) polymer. A lower poly(vinylpyrrolidone/alkylene) polymer refers to a poly(vinylpyrrolidone/alkylene) polymer having an alkylene group containing a length of about 10 carbon atoms to about 24 carbon atoms. Preferably, the lower poly(vinylpyrrolidone/alkylene) polymer has a alkylene group containing about 14 carbon atoms to about 22 carbon atoms. The higher poly(vinylpyrrolidone/alkylene) polymer has an alkylene group containing at least about 24 carbon atoms or higher. The upper level of the number of carbon atoms on the alkylene group can be provided based upon the availability of the component and the desire to provide a sunscreen composition that has flowable properties. If the number of carbon atoms on the alkylene group is too high, it is expected that the sunscreen composition may not possess desired flow. A preferred higher poly(vinylpyrrolidone/alkylene) polymer has an alkylene group containing about 24 carbon atoms to about 32 carbon atoms, and more preferably about 26 carbon atoms to about 30 carbon atoms. The selection of the lower poly(vinylpyrrolidone/alkylene) polymer and the higher poly(vinylpyrrolidone/alkylene) polymer can include the proviso that the alkylene groups are different in carbon atom length by at least four carbon atoms.

The poly(vinylpyrrolidone/alkylene) polymers that can be used according to the invention can have a molecular weight that is sufficiently high so that the polymer maintains its water insolubility but the molecular weight should not be so high that it becomes difficult to melt process the polymer. The weight average molecular weight of the poly(vinylpyrrolidone/alkylene) polymer can be about 3,000 to about 400,000.

Another way to characterize the size of the poly(vinylpyrrolidone/alkylene) polymer is by the number of repeating units (n). In the case of a poly(vinylpyrrolidone/alkylene) polymer having a weight average molecular weight of about 6,000 to about 30,000, the poly(vinylpyrrolidone/alkylene) polymer can have about 20 to about 80 repeating units, and can have about 30 to about 50 repeating units. It should be understood that repeating units refer to the residues of vinylpyrrolidone/alkylene groups.

Exemplary lower poly(vinylpyrrolidone/alkylene) polymers that can be used according to the invention include poly(vinylpyrrolidone/eicosene) and poly(vinylpyrrolidone/hexadecene). Poly(vinylpyrrolidone/eicosene) can be referred to as PVPE and is commonly used in pharmaceutical and cosmetic preparations. An exemplary form of PVPE for use according to the invention includes about 43 to 44 repeating units in length and has a weight average molecular weight of about 17,000 and can be characterized as a paraffin-like solid. This particular PVPE is highly insoluble in water, and has an extremely low oral toxicity ($LD_{50}$>17000 mg/kg) and exhibits no demonstrable dermal toxicity. Poly(vinylpyrrolidone/1-hexadecene) can be referred to as PVPH. An exemplary form of PVPH is available as a viscous yellow liquid that is insoluble in water and has a low oral toxicity ($LD_{50}$>64000 mg/kg), has about 39 to 40 repeating units, a molecular weight of about 14,000, and exhibits no demonstrable dermal toxicity.

PVPE and PVPH differ in the length of the hydrocarbon side chain, and are used extensively in the skin care industry, usually in concentrations of less than 1% by weight, because of their ability to bind to skin. Because the skin care industry generally prefers to apply actives to skin using a water-based composition, the use of PVPE and PVPH often requires solvents, surfactants, and emulsifiers to stabilize these polymers in a water emulsion. However, many of the solvents, surfactants and emulsifiers used to stabilize PVPE and PVPH in a water emulsion lack the low dermal toxicities of PVPE and PVPH. PVPE and PVPH by themselves lack a cosmetically elegant appeal when applied directly to the skin. They tend to be sticky and greasy. An exemplary higher poly(vinylpyrrolidone/alkylene) polymer includes poly(vinylpyrrolidone/tricontanyl) polymer wherein the tricontanyl group has about 30 carbon atoms. Poly(vinylpyrrolidone/tricontanyl) polymer is available under the name Ganex WP-660 from ISP.

The hydrophobic polymer composition is provided as a mixture of a lower poly(vinylpyrrolidone/alkylene) polymer (the lower polymer) and a higher poly(vinylpyrrolidone/alkylene) polymer (the higher polymer). Furthermore, either or both of the lower poly(vinylpyrrolidone/alkylene) polymer or the higher poly(vinylpyrrolidone/alkylene) polymer can be provided as mixtures. A mixture of a lower poly(vinylpyrrolidone/alkylene) polymer and a higher poly(vinylpyrrolidone/alkylene) polymer can be provided so that the weight ratio of lower to higher is sufficient to achieve the desired UV-A absorber stability, but should not be so great that the composition too difficult to process. For example, the ratio of the lower polymer to the higher polymer can be about 10:1 to about 2:1, and can preferably be about 7:1 to about 3:1. Furthermore, the lower poly(vinylpyrrolidone/alkylene) polymer can be provided as a mixture of a first poly(vinylpyrrolidone/alkylene) polymer and a second poly(vinylpyrrolidone/alkylene) polymer. An exemplary mixture of lower polymers can include a mixture of PVPH and PVPE. When PVPH and PVPE are mixed to form the lower polymer, they can be mixed at a weight ratio of PVPH to PVPE of about 4:1 to about 12:1. Preferably, the ratio of PVPH to PVPE can be about 6:1 to about 10:1.

The hydrophilic polymer composition that can be used according to the invention includes at least one hydrophilic polymer and may include a mixture of hydrophilic polymers. The hydrophilic polymers that can be used according to the invention include polymers having repeating carboxylic acid groups and/or hydroxyl groups. Exemplary hydrophilic polymers that can be used according to the invention include polyacrylic acid polymers and poly(maleic acid/methylvinylether) copolymers. The hydrophilic polymers should have a molecular weight that is not too high so that the hydrophilic polymer becomes difficult to process.

Polyacrylic acid polymers that can be used according to the invention include those having a weight average molecular weight of at least about 50,000. Polyacrylic acid polymers that can be used include those having a weight average molecular weight between about 50,000 and about 4,000,000. The polyacrylic acid polymers can have a level of cross-linking that is less than about 1%. A general structural representation of polyacrylic acid polymers is shown below:

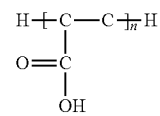

wherein n is the number of repeating units. The number n can be between about 1,000 and about 20,000.

Poly(maleic acid/methylvinylether) copolymers that can be used according to the invention can have a weight average molecular weight of at least about 50,000, and can have a weight average molecular weight of between about 50,000 and about 4,000,000. The weight average molecular weight can be between about 70,000 and 2,500,000. A general structural representation of poly(maleic acid/methylvinylether) copolymers is shown below:

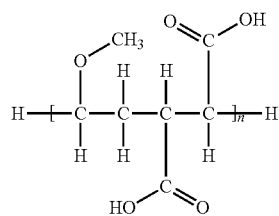

wherein n is the number of repeating units. The number n can be between about 200 and about 20,000.

Additional hydrophilic polymers that can be used according to the invention include starch, derivatives of starch, polyvinyl alcohol, cellulose, derivatives of cellulose, carboxymethyl cellulose, cyclodextrins, and dextrans. The weight average molecular weight of the hydrophilic polymers is preferably sufficient to provide solubility in water but not too high to become difficult to process. Exemplary starches include amylopectin and polyglucose. Starches that can be used according to the invention can have a weight average molecular weight of about 50,000 to about 20,000,000. A derivative of starch that can be used according to the invention includes partially hydrolyzed starch. Cellulose that can be used according to the invention can have a weight average molecular weight of about 50,000 to about 15,000,000. Polyglucose that can be used according to the invention can be characterized as low fraction polyglucose having a weight average molecular weight of about 60,000 to about 90,000, and high fraction polyglucose having a weight average molecular weight of about 90,000 to about 300,000. An exemplary low fraction polyglucose material that can be used according to the invention is available under the name Dextran-70. In general, this type of polyglucose has all alpha 1-6 linkages. Starch derivatives that can be used according to the invention include those starch derivatives having alpha 1-4 linkages. An example of this type of starch derivative includes cyclodextrins. Exemplary cyclodextrins that can be used according to the invention include those that act to provide a cavity within the molecule large enough to contain components desirable for topical applications. Cyclodextrins that can be used according to the invention can have a molecular weight of about 900 to about 1,400. Polyvinyl alcohols that can be used according to the invention include those with a weight average molecular weight of about 50,000 to about 200,000.

Exemplary hydrophilic polymers that can be used according to the invention include those polymers having the following melting temperature range and the following maximum temperature range beyond which it is expected decomposition of the polymer will occur. Exemplary poly(maleic acid/methylvinylether) copolymers that can be used include those having a melting temperature range of about 60° C. to about 65° C. and a maximum temperature range of about 80° C. to about 90° C. Exemplary polyacrylic acid polymers that can be used include those having a melting temperature range of about 65° C. to about 70° C. and a maximum temperature range of about 80° C. to about 90° C. Exemplary carboxymethyl cellulose polymers that can be used include those having a melting temperature range of about 55° C. to about 60° C. and a maximum temperature range of about 75° C. to about 80° C. Exemplary polyvinyl alcohol polymers that can be used include those having a melting temperature range of about 50° C. to about 55° C. and a maximum temperature range of about 65° C. to about 70° C. Exemplary starches that can be used include those having a melting temperature range of about 40° C. to about 45° C. and a maximum temperature range of about 50° C. to about 55° C. Exemplary dextrans that can be used include those having a melting temperature range of about 37° C. to about 40° C. and a maximum temperature range of about 45° C. to about 50° C. Exemplary β-cyclodextrins that can be used according to the invention include those having a melting temperature range of about 40° C. to about 45° C. and a maximum temperature range of about 65° C. to about 70° C.

The hydrophobic polymer composition and the hydrophilic polymer composition can be combined and heated to at least about 50° C. to provide a polymer melt. The composition can be heated to at least about 125° C. under mixing to form complexes between the hydrophobic and hydrophilic polymers. It should be understood that a polymer melt refers to a polymer that flows or becomes a liquid when heated and is not meant to refer to a polymer that forms a liquid as a result of being dissolved in a solvent.

The complex formation step can be carried out in a relatively anhydrous environment. That is, the amount of water provided in the composition during the complex formation step can be less than about 1 wt. %. Once the desired level of complex formation has occurred, the composition can be hydrated with water.

The hydrophobic polymer composition and the hydrophilic polymer composition can be mixed together in amounts sufficient to provide a ratio of pyrrolidone groups to the combination of carboxylic acid groups and hydroxyl groups of about 1:1 to about 5:1. The ratio of the structures causing the observed interaction between the hydrophobic polymer composition and the hydrophilic polymer composition can be referred to as "functional group parity." The ratio of pyrrolidone groups to the combination of carboxylic acid groups and hydroxyl groups can be about 1.5:1 to about 3:1. In order to drive the complex formation reaction, it is desirable to provide an imbalance between the two types of groups. Accordingly, it is generally desirable to provide more of the pyrrolidone groups than the combination of carboxylic groups and the hydroxyl groups. It should be understood that the reference to a "combination of carboxylic groups and hydroxyl groups" refers to the total amount of carboxylic groups and hydroxyl groups present but does not require the presence of both carboxylic groups and hydroxyl groups. For example, the value of the combination of carboxylic groups and hydroxyl groups can be determined for a composition that contains only carboxylic groups. Similarly, the value can be determined for a composition that contains only hydroxyl groups.

During the complex formation step, the amounts of hydrophobic polymer composition and hydrophilic polymer composition can be characterized on a weight percent basis. For example, about 2 wt. % to about 28 wt. % hydrophilic polymer composition and about 72 wt. % to about 98 wt. % hydrophobic polymer composition can be combined to provide for complex formation. About 8 wt. % to about 25 wt. % hydrophilic polymer composition and about 72 wt. % to about 95 wt. % hydrophobic polymer composition can be combined to form the complex. During the complex formation step, the amount of water available in the composition can be less than about 1 wt. %. Although the complex forming composition can be relatively anhydrous, it is expected that the amount of water can be about 0.3 wt. % to about 1.0 wt. %.

Once the hydrophobic polymers and the hydrophilic polymers have sufficiently reacted or interacted to form a complex, water can be added to the composition to provide a stable aqueous composition that can be relatively easily further hydrated. It has been found that the first hydration of the topical composition precursor is the most difficult hydration step because of the need to control the conditions of hydration. After the first hydration to a water content of at least about 30 wt. %, it is expected that further hydrations to higher water contents are relatively easy and can be accomplished by simply mixing the composition with water. Accordingly, the amount of water provided in the composition when made available as a concentrate for shipment is preferably between about 30 wt. % and about 45 wt. %. When the composition includes about 30 wt. % to about 45 wt. % water, it is expected that the composition will include between about 3 wt. % and about 10 wt. % hydrophilic polymer composition and between about 30 wt. % and about 50 wt. % hydrophobic polymer composition.

Water can be added to the relatively anhydrous composition by mixing water and the relatively anhydrous composition at a temperature and for a time sufficient to allow the composition to become hydrated without losing significant amounts of interaction between the hydrophobic polymer composition and the hydrophilic polymer composition. The relatively anhydrous composition can be hydrated by heating to at least 60° C. and adding water while mixing. The composition can be heated to at least about 65° C. and to at least about 70° C. An exemplary temperature range is about 65° C. to about 80° C.

The relatively anhydrous composition can be referred to as the topical composition precursor and generally refers to the hydrophobic polymer/hydrophilic polymer adduct. The polymer component for the sunscreen composition can refer to a composition that contains only the hydrophobic polymer/hydrophilic polymer adduct, and it can refer to a composition wherein the hydrophobic polymer/hydrophilic polymer adduct is diluted with water. In general, it is desirable to have a sufficient amount of water in the polymer component that allows one to formulate the polymer component into the sunscreen composition according to the invention. If there is too little water in the polymer component, it may become difficult to formulate the sunscreen composition. For example, the polymer component can contain water in an amount of up to about 95 wt. %. The polymer component can have a water concentration of between about 30 wt. % to about 45 wt. %.

Sunscreen Agent

The sunscreen composition according to the invention can contain a sunscreening effective amount of a sunscreen agent. Exemplary sunscreen active ingredients include one or more UV-A absorbers, UV-B absorbers, and mixtures of UV-A absorbers and UV-B absorbers. UV-A absorbers protect against long wavelength actinic radiation of the sun in the 320 to 400 nm range and UV-B absorbers protect against shorter wavelength actinic radiation of the sun in the 280-320 nm range.

The sunscreen includes a sufficient amount of the sunscreen agent to provide the desired SPF value. SPF values refer to those values obtained with methods based upon the test procedures proposed to the Title 21 of the United States Code of Federal Regulations, §§352.72, pages 27690 through 27693 (final monograph).

Sunscreen agent that can be used according to the invention include any of the sunscreen agent that provide desired protection from the sun's radiation and that are approved for use in a composition that contacts skin tissue. Exemplary sunscreen agents include para-aminobenzoic acid (PABA) up to about 15 weight percent or from about 5 to 15 weight percent in admixture with other sunscreen agent; cinoxate up to about 3 weight percent or about 1 to 3 weight percent in admixture; diethanolamine methoxycinnamate up to 10 weight percent or about 8 to 10 weight percent in admixture; digalloyl trioleate up to 5 weight percent or about 2 to 5 weight percent in admixture; dioxybenzone up to 3 weight percent alone or in admixture; ethyl 4-[bis(hydroxypropyl)]aminobenzoate up to 5 weight percent or about 1 to 5 weight percent in admixture; glyceryl aminobenzoate up to 3 weight percent or about 2 to 3 weight percent in admixture; homosalate up to 15 weight percent or about 4 to 15 weight percent in admixture; lawsone up to 0.25 weight percent with dihydroxyacetone up to 3 weight percent; menthyl anthranilate up to 5 weight percent or about 3.5 to 5 weight percent in admixture; octocrylene up to 10 weight percent or 7 to about 10 weight percent in admixture; octyl methoxycinnamate up to 7.5 weight percent or about 2 to 7.5 weight percent in admixture; octyl salicylate up to 5 weight percent or about 3 to 5 weight percent in admixture; oxybenzone up to 6 weight percent or about 2 to 6 weight percent in admixture; padimate "O" up to 8 weight percent or about 1.4 to 8 weight percent in admixture; phenylbenzimidazole sulfonic acid up to 4 weight percent or about 1 to about 4 weight percent admixture; red veterinary petrolatum up to 95 percent or about 30 to 95 weight percent in admixture; sulisobenzone up to 10 weight percent or about 5 to 10 weight percent in admixture; titanium dioxide up to 25 weight percent or about 2 to 25 weight percent in admixture; trolamine salicylate up to 12 weight percent or about 5 to 12 weight percent in admixture; avobenzone up to 3 weight percent; and zinc oxide up to 25 weight percent.

Typical suitable UV-B type absorbers include benzophenone-3, benzophenone-8, substituted para-aminobenzoates, e.g. alkyl esters of para-methoxycinnamate, octyl methoxycinnamate and octyl para-methoxycinnamate, available from Givaudan Corp., Clifton, N.J. 07104 under the tradename Parsol MCX and usually present in the range of about 2 to 7.5 weight percent or octyl salicylate available from Harmann and Riemer, Springfield, N.J. 07081, usually in the range of about 3 to 5 weight percent.

Typical suitable UV-A type absorbers include oxybenzone, usually in the range of about 2 to about 6 weight percent. Another exemplary UV-A absorber is avobenzone and is available under the name Parsol 1789. Avobenzone can be used in an amount of about 0.5 wt. % to about 3 wt. %, and can be used in an amount of about 1 wt. % to about 3 wt. %. Another exemplary UV-A absorber is oxybenzophenone. Oxybenzophenone can be used in an amount of about 0.5 wt. % to about 6 wt. %, and can be used in an amount of about 1 wt. % to about 6 wt. %. Another exemplary UV-A absorber is octocrylene. Octocrylene can be used in an amount of about 0.5 wt. % to about 10 wt. %, and can be use in an amount of about 1 wt. % to about 10 wt. %. UV-A absorbers have a tendency to degrade in the presence of light. As a result of the degradation, UV-A absorbers tend to lose their ability to filter UV-A radiation. The sunscreen composition provides for enhancing the stability of UV-A absorbers in general, thereby enhancing the effectiveness of the sunscreen composition for filter UV-A radiation. In particular, the sunscreen composition provides for enhancing the stability of avobenzone.

Except as noted otherwise, one or more sunscreen agent can be employed in the present composition in amounts up to 35 weight percent, and in amounts of about 2 to about 30 weight percent, based on the weight of the sunscreen.

pH Adjusting Agent

The sunscreen composition can include a pH adjusting agent to provide the sunscreen composition with a pH that helps stabilize the sunscreen agent. By maintaining certain sunscreen agents, such as dihydroxyacetone (DHA) or 1,3,4-trihydroxy-2-butanone, in a composition at a pH below about 5. Exemplary pH adjusting agents that can be used include citric acid, lactic acid, acetic acid, propionic acid, and mixtures thereof.

Water

The sunscreen composition can include water in an amount sufficient to allow the composition to be applied to skin tissue while providing the desired coverage of the sunscreen agent over the skin tissue. The water component can be provided as deionized water, filtered water, distilled water, reverse osmosis water, or tap water. In the event that the water includes hardness or other components, it may be desirable to include builders, sequestrants, and chelating agents to handle the water hardness. In general, the sunscreen composition can include at least about 50 wt. % water. In addition, it is expected that if there is too much water, the emulsion might become unstable. In general, the amount of water in the sunscreen composition can be less than about 95 wt. %. The amount of water in the sunscreen composition can be about 65 wt. % to about 93 wt. %.

Surfactant Component

The sunscreen composition can include a surfactant component to help maintain the composition as an emulsion. In general, an emulsion refers to a composition that resists phase separation after sitting at room temperature for a couple of months. In general, it is expected that the sunscreen composition can be stored in a warehouse or in a storage closet for at least two months and can remain as an emulsion during that two month period. Preferably, the sunscreen composition can remain as an emulsion for at least one year or at least two years. The ability of the sunscreen composition to remain as an emulsion can be tested according to an accelerated stability test where the composition is held at 45° C. for four months. It is expected that this accelerated stability test for four months roughly corresponds to a period of about two years at room temperature. In general, it is expected that the sunscreen composition will remain as an emulsion after sitting for two month at 45° C. and preferably at least four months at 45° C.

Exemplary surfactants that can be used as the surfactant component include nonionic surfactants that help stabilize the emulsion, wet skin tissue, and provide a generally even distribution of the sunscreen agent. Exemplary nonionic surfactants that can be used include glycerol stearate such as glycerol monostearate, polysorbate such as that available under the name Tween 60, and polyoxyethylene stearate. In addition, mixtures of nonionic surfactants can be included including mixtures of polysorbate and glycerol stearate.

It is believed that anionic surfactants may be useful as part of the surfactant component. In general, it is expected that anionic surfactants have a greater tendency to cause irritation to skin tissue.

The sunscreen composition can include an amount of surfactant component sufficient to provide the composition with a desired emulsion stability and sufficiently low viscosity without foaming. The amount of the surfactant component in the sunscreen composition, if present at all, can be about 1 wt. % to about 6 wt. %, and can be about 2 wt. % to about 5 wt. %. Preferably, the sunscreen composition contains no surfactant or zero amount of surfactant because surfactants have a tendency to decrease binding of the composition to the skin tissue. The composition can contain substantially no surfactant meaning that the composition can contain surfactant but not an amount of surfactant that significantly decreases the effectiveness of the composition for binding to skin tissue.

Thickener

Thickeners that can be incorporated into the sunscreen composition include those components that thicken or increase the viscosity of the sunscreen composition so that the sunscreen composition can be readily applied to skin. Thickeners that can be used in the sunscreen composition include those components often referred to as viscosity controlling agents.

Exemplary thickeners or viscosity controlling agents that can be provided in the sunscreen composition include cellulose gum, alkane triols; acrylates; substituted celluloses such as methylcellulose, and hydroxypropyl cellulose; cetyl alcohol; gums such as natural gums or synthetic gums; long chain alcohols such as those having about 9 to about 24 carbon atoms; polyglycols such as polyethylene glycols, polypropylene glycols, polybutylene glycols, polyethylene propylene glycols, or mixtures thereof; waxes such as natural waxes or synthetic waxes; hydrogenated oils; glycol esters; fatty acid esters; long chain acids; acid amides; silicates; and mixtures thereof. An exemplary thickener that can be used is hydroxyethyl cellulose.

The sunscreen composition may or may not include a thickener. When the sunscreen composition includes a thickener, the thickener can be provided in an amount that provides the desired level of thickening. The sunscreen composition can include a thickener in an amount of least about 0.1 wt. % and can include a thickener in an amount of at least about 0.4 wt. %. In addition, the thickener can be provided in an amount of less than about 2 wt. %, and can be provided in an amount of less than about 1.0 wt. %.

Emollient

The sunscreen composition can include an emollient for improving the texture of the composition. An emollient is an oleaginous or oily substance which helps to smooth and soften the skin, and may also reduce its roughness, cracking or irritation. Typical suitable emollients include mineral oil, having a viscosity in the range of 50 to 500 centipoise (cps), lanolin oil, coconut oil, cocoa butter, olive oil, almond oil, macadamia nut oil, synthetic jojoba oils, natural sonora jojoba oils, safflower oil, corn oil, liquid lanolin, cottonseed oil and peanut oil.

Other suitable emollients include squalane, castor oil, polybutene, odorless mineral spirits, sweet almond oil, avocado oil, clophyllum oil, ricin oil, vitamin E acetate, olive oil, linolenic alcohol, oleyl alcohol, the oil of cereal germs such as the oil of wheat germ, isopropyl palmitate, octyl palmitate which is commercially available as Lexol EHP, tradename of Inolex Co. of Philadelphia, Pa., isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other suitable emollients which are solids or semi-solids at room or ambient temperatures may be used in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. Exemplary emollients include stearic acid, cetyl alcohol, natural and synthetic esters such as coconut oil. The sunscreen composition can include the emollient in an amount sufficient to provide a silky feel. An exemplary range of the emollient in the sunscreen composition can be at least about 0.5 wt. %. In addition, the sunscreen composition can include an emollient in an amount of less than about 3 wt. %. It should be understood that the emollient is an optional component of the sunscreen composition.

Moisturizer

The sunscreen composition can include a moisturizer to provide a desired moisturizing effect to skin tissue. The moisturizer can be provided as a humectant. In general, a humectant is a moistening agent that promotes retention of water due to its hydroscopic properties. Exemplary humectants include glycerine, polymeric glycols such as polyethylene glycol and polypropylene glycol, and sorbitols such as sorbitol solution, pyrrolidone carboxylic acid, urea, or mixtures thereof. The sunscreen composition can be provided without a moisturizer. When the sunscreen composition includes a moisturizer, it can be included in an amount of at least about 0.5 wt. %. In addition, the sunscreen composition can include a moisturizer in an amount of less than about 5 wt. %.

Coloring Agent

The sunscreen composition can, if desired, include a colorant or coloring agent such as a dye, pigment, or tint. In general, it is expected that a coloring agent may be useful to help gauge application of an even coating of the sunscreen composition to skin tissue.

Exemplary coloring agents include certified dyes that are synthetic organic coal tar derivatives which are manufactured so that each batch passes a Food & Drug Administration (FDA) purity inspection. If approved by the FDA, these dyes are certified for use in foods, drugs, cosmetics (FDA colors), drugs and foods only (DC colors), or in topically applied drugs and cosmetics (External DC colors). Certified dyes can be water soluble or lakes. Lakes are organic pigments prepared by precipitating a soluble dye on a reactive or absorbent stratum which is an essential part of the pigment's composition. Most lakes are aluminum, barium or calcium derived. These insoluble pigments are used mostly in makeup products, either powders or liquids, when a temporary color is desired that will not stain the skin (as oil-soluble dyes tend to do). The lakes can be used along with inorganic colors such as iron oxide, zinc oxide, and titanium dioxide (the whitest white pigment).

Water soluble, certified dyes can be used. When incorporating these dyes in an emulsion, they will be soluble in the external water phase in an oil/water system. It is useful to know the solubility properties of the certified dyes in various solvents and their stability to reactive chemicals. Table I lists some of the currently available water soluble certified dyes.

TABLE I

Water-Soluble Dyes

FDC Blue #1
FDC Blue #2
FDC Green #3
FDC Red #3
FDC Red #40
FDC Yellow #5
FDC Yellow #6
DC Green #5
DC Red #22
DC Red #28
DC Red #33
DC Yellow #10
Ext DC Violet #2
Ext DC Yellow #7
DC Green #8
DC Orange #4
DC Yellow #8

The water-soluble color dye can also be a natural color such as caramel color or walnut see extract color.

The sunscreen composition can contain the water-soluble color dye (color indicator) in an amount sufficient to enable the composition to be readily visualized (i.e. colored) when initially applied to the skin, such that when the emulsion dries after being spread on the skin and/or is rubbed out using one's hand and/or fingers, the color substantially disappears.

If the sunscreen composition includes a coloring agent, it can be included in an amount sufficient to provide the desired amount of coloring. One or more coloring agents can be used in the composition in an amount of about 0.00001 to about 0.5% by weight of the composition. In addition, it can be used in an amount of about 0.0001 to about 0.2%, and in an amount of about 0.001 to about 0.1%. It should be understood that the sunscreen composition can be provided without a coloring agent.

Preservatives

The sunscreen composition can include preservatives for prevention of bacterial, fungal, and/or yeast contamination. Exemplary preservatives that can be used in the sunscreen composition include phenoxyethanol, benzoic acid, derivatives and salts of benzoic acid, parabens, oxazolidines, chlorinated aromatic compounds and phenols, hydantoins, cresols and derivatives, imiazolindinyl urea, iodopropanol butylcarbamate, sulfites, and bisulfites. The sunscreen composition can include any of the preservatives commonly used or known to be suitable for topically applied compositions.

The sunscreen composition can be formulated without a preservative. It is expected that the preservative will increase the shelf life of the sunscreen composition by reducing or preventing the growth of bacteria, fungus, and/or yeast. When the sunscreen composition includes a preservative, the preservative is preferably provided in an amount sufficient to provide a desired level of protection from growth of bacteria, fungus, and/or yeast. In general, for most preservatives, it is expected that the amount of preservative will be provided at a level of between about 0.25 wt. % and about 1.0 wt. %, and can be provided at a level of between about 0.3 wt. % and about 0.5 wt. %, based on the weight of the sunscreen composition.

Antioxidants

The sunscreen composition can include antioxidants to help increase the shelf life of the sunscreen composition by reducing oxidation of the skin coloring agent. Exemplary antioxidants that can be used include vitamins such as vitamin E, vitamin E acetate, vitamin C, vitamin A, and vitamin D, and derivatives thereof. Exemplary antioxidants include α-tocopherols which can be characterized as natural or synthetic Vitamin E. Additional exemplary antioxidants include propyl, octyl and dodecyl esters of gallic acid, butylated hydroxyanisole (BHA) (usually as a mixture of ortho and meta isomers), butylated hydroxytoluene (BHT), and nordihydroguaiaretic acid, and alkylated parabens such as methylparaben and propylparaben.

The sunscreen composition can be formulated without an antioxidant. When the sunscreen composition includes an antioxidant, the antioxidant is preferably provided in an amount that provides antioxidant properties in the sunscreen composition. In general, it is expect that the antioxidant can be provided in an amount of between about 0.2 wt. % and about 2 wt. %, and can be provided in an amount of between about 0.7 wt. % and about 1.5 wt. %, based on the weight of the sunscreen composition. In the case of vitamin E, it is expected that the vitamin E can be included in the sunscreen composition in an amount of about 0.1 wt. % to about 1 wt. %, and can be included in an amount of about 0.3 wt. % to about 0.8 wt. %.

One or more antioxidants can optionally be included in the emulsion in an amount ranging from about 0.001 to about 5 weight percent, preferably about 0.05 to about 2 percent. It should be appreciated that the sunscreen composition can be provided without an antioxidant.

Chelating Agents

Chelating agents are substances used to chelate or bind metallic ions with a certain heterocyclic ring structure so that the ion is held by chemical bonds from each of the participating rings. Suitable chelating agents include ethylene diaminetetraacetic acid (EDTA), EDTA trisodium, EDTA tetrasodium, calcium disodium edetate, EDTA trisodium, EDTA tetrasodium and EDTA dipotassium. One or more chelating agents can optionally be included in the emulsion in amounts ranging from about 0.001 to about 0.1 weight percent. It should be appreciated that the sunscreen composition can be provided without a chelating agent.

Fragrances

Fragrances are aromatic compounds which can impart an aesthetically pleasing aroma. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. One or more fragrances can optionally be included in the composition in an amount ranging from about 0.001 to about 10 weight percent, preferably about 0.05 to about 5 percent. It should be appreciated that the sunscreen composition can be provided without a fragrance.

The sunscreen composition can be provided without or with limited amounts of certain types of components commonly found in conventional sunscreen compositions. For example, alcohols can be excluded from the sunscreen composition. Alternatively, alcohols can be limited to an amount of less than about 1 wt. %. Organic solvents can be excluded from the sunscreen composition or can be limited to an amount of less than 5 wt. %. Silicones can be excluded from the composition or can be limited to an amount of less than about 1 wt. %. Surfactants can be excluded from the composition or can be limited to amount of less than about 0.5 wt. % or less than about 0.1 wt. %. Greater amounts of these components can be incorporated into the sunscreen composition, if desired.

EXAMPLE 1

A sunscreen composition was prepared and tested to evaluate photostability. The sunscreen composition was prepared from a sunscreen base having the following formulation:
  42.44 wt. % water
  5 wt. % poly(maleic acid/methylvinylether) copolymer
  46.46 wt. % poly(vinylpyrrolidone/hexadecene) polymer
  5.6 wt. % poly(vinylpyrrolidone/eicosene) polymer
  0.5 wt. % preservative The preparation was made by mixing the poly(vinylpyrrolidone/hexadecene) polymer and poly(vinylpyrrolidone/eicosene) polymer together and heating to 110° C. Poly(maleic acid/methylvinylether) copolymer was then added, and the mixture was cooled to 80° C. Water and preservative were added and the mixture was cooled with stirring.

The composition contains 3 wt. % avobenzone, 6 wt. % octocrylene, and 4 wt. % oxybenzophenone. The calculated SPF of this composition is 25.

To test the photostability of the sunscreen composition, 200-250 μl of the sunscreen composition was spread evenly over a 25 cm$^2$ piece of polyethylene film. The amount of sunscreen preparation was determined by weight, and the polyethylene film was dried for 1 hour at 35° C. After drying the film was exposed to 18.6 Watts (2340 Watts/m$^2$) of UV light at 365 nm for 0, 2, 4, 6 and 8 hours. Following light exposure, sunscreen was extracted with ethanol containing 1% acetic acid. Extracts were separated and quantitated with a C18 column with a methanol:water linear gradient. Results are shown in FIG. 1.

The three sunscreen agents in this preparation decreased in concentration and hence SPF value over the time of exposure. None declined as much as avobenzone, losing nearly 50% between 4 and 8 hours of UV exposure.

EXAMPLE 2

Example 1 was repeated with the exception that the sunscreen base was modified. The sunscreen composition was prepared from a sunscreen base having the following formulation:
  43.04 wt. % water
  5 wt. % poly(maleic acid/methylvinylether) copolymer
  37.46 wt. % poly(vinylpyrrolidone/hexadecene) polymer
  5 wt. % poly(vinylpyrrolidone/eicosene) polymer
  9 wt. % poly(vinylpyrrolidone/tricontanyl) polymer
  0.5 wt. % preservative The preparation was made by mixing the poly(vinylpyrrolidone/hexadecene) polymer, poly(vinylpyrrolidone/eicosene) polymer, and poly(vinylpyrrolidone/tricontanyl) polymer together and heating to 110° C. Poly(maleic acid/methylvinylether) was then added, and the mixture was cooled to 80° C. Water and preservative were added and the mixture was cooled with stirring.

Figure 2:
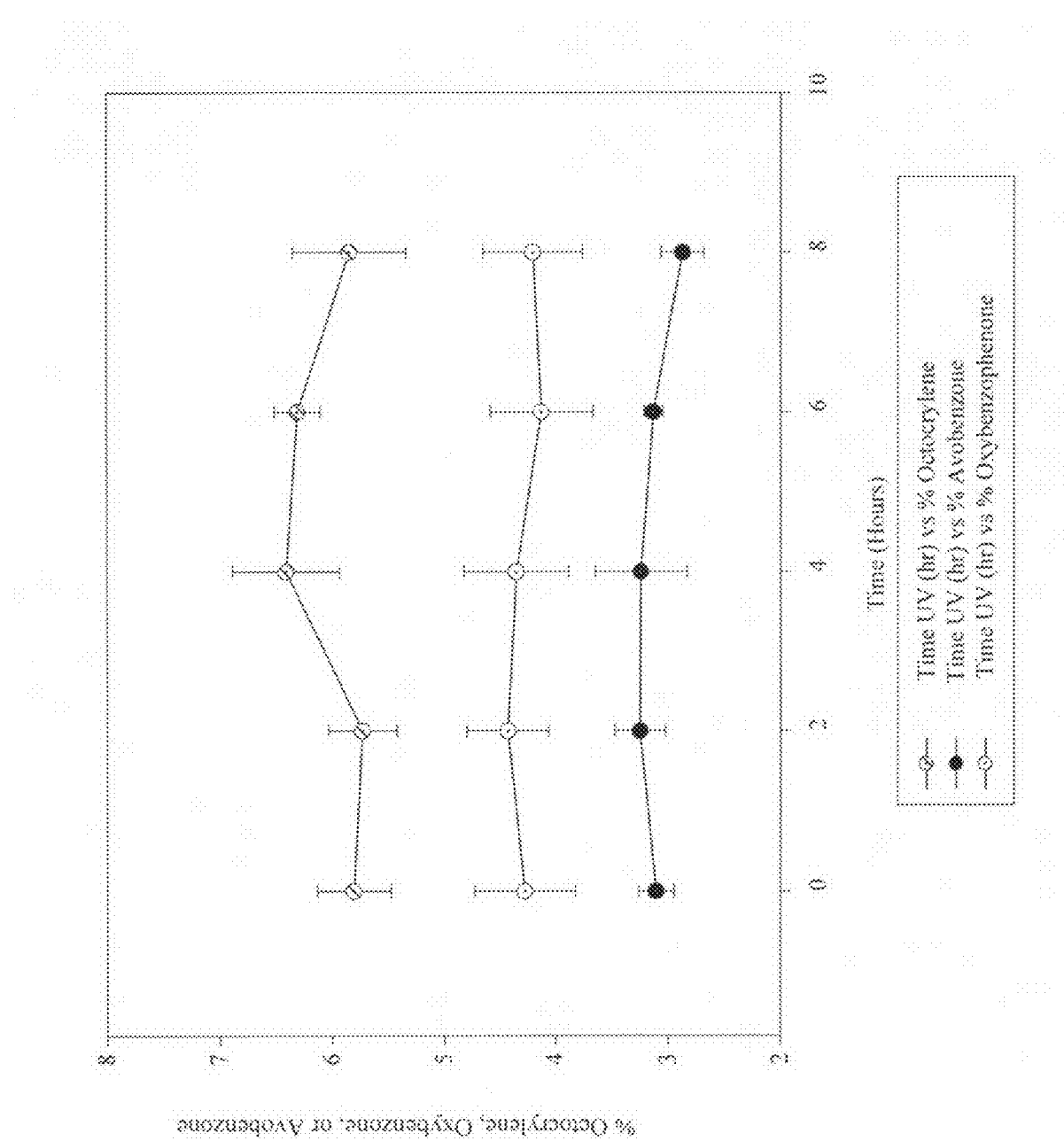
FIG. 2 is a graph of photostability of oxybenzophenone, octocrylene, and avobenzone with UV exposure.

The composition contains 3 wt. % avobenzone, 6 wt. % octocrylene, and 4 wt. % oxybenzophenone as sunscreen agents. Photo stability test of the composition was carried out as described in Example 1. The results of the photo stability testing are shown in FIG. 2.

Clearly no photo degradation of any of the sunscreen agents is apparent during the eight hours of UV exposure. To verify the photo stability results, samples of all sunscreen preparations were sent to an independent laboratory for solar light equivalent exposure under I.C.H. guidelines. All samples were exposed to 1,000,000 lumens of solar equivalent light. Subsequent chromatography of the samples showed no degradation of the sunscreens in the PVMMA VP/hexadecane VP/eicosene PVP/tricontanyl preparations.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A sunscreen composition comprising:
   (a) a skin bonding polymer composition comprising a hydrophobic polymer/hydrophilic polymer adduct, wherein the hydrophobic polymer/hydrophilic polymer adduct comprises:
      (i) a hydrophobic polymer composition comprising a mixture of a lower poly(vinylpyrrolidone/alkylene) polymer wherein the alkylene group contains 10 to 24 carbon atoms and a higher poly(vinylpyrrolidone/alkylene) polymer wherein the alkylene group contains about 30 carbon atoms; and
      (ii) a hydrophilic polymer composition comprising poly(maleic acid/methylvinylether) copolymer having a weight average molecular weight of at least 50,000; and
      (iii) wherein the weight ratio of the lower poly(vinylpyrrolidone/alkylene) polymer to the higher poly(vinylpyrrolidone/alkylene) polymer is about 10:1 to about 2:1;
   (b) sunscreen active agent comprising a UV-A absorber; and
   (c) water in an amount effective to provide the composition with a texture suitable for application to skin.

2. A sunscreen composition according to claim 1, wherein the hydrophobic polymer/hydrophilic polymer adduct comprises a result of melt mixing the lower poly(vinylpyrrolidone/alkylene) polymer, the higher poly(vinylpyrrolidone/alkylene) polymer, and the hydrophilic polymer composition.

3. A sunscreen composition according to claim 1, wherein the lower poly(vinylpyrrolidone/alkylene) polymer comprises poly(vinylpyrrolidone/hexadecene) polymer, poly(vinylpyrrolidone/eicosene) polymer, or a mixture of poly(vinylpyrrolidone/hexadecene) polymer and poly(vinylpyrrolidone/eicosene) polymer.

4. A sunscreen composition according to claim 1, wherein the higher poly(vinylpyrrolidone/alkylene) polymer comprises poly(vinylpyrrolidone/tricontanyl) polymer.

5. A sunscreen composition according to claim 1, wherein the hydrophobic polymer composition and the hydrophilic polymer composition have a functional group parity provided at a ratio of about 1:1 to about 5:1.

6. A sunscreen composition according to claim 1, wherein the hydrophobic polymer composition and the hydrophilic polymer composition have a functional group parity provided at a ratio of about 1.5:1 to about 3:1.

7. A sunscreen composition according to claim 1, wherein the UV-A absorber comprises oxybenzophenone, octocrylene, or avobenzone.

8. A sunscreen composition according to claim 1, wherein the composition comprises about 1 wt. % to about 30 wt. % of the at least one UV-A absorber.

9. A sunscreen composition according to claim 1, wherein the water is provided at a concentration of about 40 wt. % to about 80 wt. % water.

10. A sunscreen composition according to claim 1, wherein the skin bonding polymer composition comprises at least 50 wt. % of the hydrophobic polymer/hydrophilic polymer adduct.

11. A sunscreen composition according to claim 1, further comprising about 0.1 wt. % to about 2 wt. % of a thickener.

12. A sunscreen composition according to claim 1, further comprising about 0.25 wt. % to about 0.5 wt. % of a preservative.

13. A sunscreen composition according to claim 1, further comprising about 0.5 wt. % to about 3 wt. % of an emollient.

14. A sunscreen composition according to claim 1, wherein the composition contains less than 1 wt. % alcohol.

15. A sunscreen composition according to claim 1, wherein the weight ratio of the lower poly(vinylpyrrolidone/alkylene) polymer to the higher poly(vinylpyrrolidone/alkylene) polymer is about 7:1 to about 3:1.

16. A sunscreen composition according to claim 1, wherein the lower poly(vinylpyrrolidone/alkylene) polymer comprises a mixture of a first poly(vinylpyrrolidone/alkylene) polymer and a second poly(vinylpyrrolidone/alkylene) polymer wherein the first poly(vinylpyrrolidone/alkylene) polymer and the second poly(vinylpyrrolidone/alkylene) polymer are different.

17. A sunscreen composition according to claim 1, wherein the lower poly(vinylpyrrolidone/alkylene) polymer has an alkylene group containing 14 to 22 carbon atoms.

18. A sunscreen composition according to claim 1, wherein the UV-A absorber has a maximum UV absorption in the UV-A range of 320-400 nm.

19. A sunscreen composition according to claim 1, wherein the composition comprises about 2 wt. % to about 30 wt. % of the sunscreen agent.

* * * * *